United States Patent [19]

Milstein et al.

[11] Patent Number: 5,106,482

[45] Date of Patent: Apr. 21, 1992

[54] HIGH SPEED OXYGEN SENSOR

[75] Inventors: Joseph B. Milstein, Brighton, Mass.; Ephraim S. Greenberg, 1 Strathmore Rd., Brookline, Mass. 02146

[73] Assignee: Ephraim S. Greenberg, Brookline, Mass.

[21] Appl. No.: 342,116

[22] Filed: Apr. 24, 1989

[51] Int. Cl.$^5$ .......................................... G01N 27/26
[52] U.S. Cl. .............................. 204/431; 204/153.16; 204/432
[58] Field of Search ............... 204/1 T, 1 P, 1 Y, 415, 204/431, 432, 153.16, 153.17

[56] References Cited

U.S. PATENT DOCUMENTS

| | | | |
|---|---|---|---|
| 2,943,028 | 6/1960 | Thayer et al. | 204/409 |
| 2,991,412 | 7/1961 | Kordesch | 204/432 |
| 3,223,597 | 12/1965 | Hersch | 204/1 Y |
| 3,793,158 | 2/1974 | Hamilton | 204/153.16 |
| 3,795,589 | 3/1974 | Dahms | 204/415 |
| 3,857,760 | 12/1974 | Breuer et al. | 240/431 |
| 4,085,024 | 4/1978 | Lawson | 204/1 Y |

OTHER PUBLICATIONS

Hackh's Chemical Dictionary, (1969), p. 221.

Primary Examiner—T. Tung
Attorney, Agent, or Firm—Herbert L. Bello

[57] ABSTRACT

An oxygen sensor or cell for measuring the oxygen content of a specimen includes a body with a chamber that houses an electrochemically active anode and an electrochemically active cathode. A chemically inert, electrically inactive porous material is dispsoed between and in contact with the anode and cathode. An anode connector is in contact with the anode and a cathode connector is in contact with the cathode. An electrolytic solution of potassium hydroxide and a dissolved metal saturates the porous material and makes electrical connection between the anode and cathode. A specimen to be measured is introduced into the chamber. The electrolyte promotes catalytic reduction of free oxygen molecules carried by the specimen. The magnitude of current flow through a resistive load connected between the anode and cathode connectors is directly proportional to the quantity of oxygen present in the specimen.

11 Claims, 2 Drawing Sheets

HIGH SPEED OXYGEN SENSOR

BACKGROUND OF THE INVENTION

1. Field of the Invention

The present invention relates to oxygen sensors and, more particularly, is directed toward a method and apparatus involving high speed sensing of oxygen.

2. Description of the Prior Art

A variety of oxygen sensors have been developed to detect and measure the oxygen content of blood samples and physiological gas samples. Typical examples of prior art oxygen sensors are described in U.S. Pat. Nos. 3,223,597, 4,042,465 and 4,085,024 and the references cited therein. One major application for prior art oxygen sensors is in the medical field, for example, in clinical medicine for use in the cardiac catheterization laboratory and cardiac surgery for measurement of oxygen in blood and gases. Another application for oxygen sensors is in the industrial field, for example, in manufacturing processes that require measurement of oxygen such as in the brewing of beer, manufacturing of paint, dyes and the like.

Currently, oxygen cells and sensors that are capable of accurately detecting and measuring oxygen content in a fluid or gas suffer from the disadvantage that they require a relatively long period of time to complete a single measurement. For example, in blood it takes approximately four minutes for a sensor to complete a single measurement. Three minutes are used for sampling and one minute is used to recondition the cell. In certain cardiac catherization procedures, it may be necessary or desirable to measure up to two dozen separate blood samples from various sites in the heart for complete diagnosis. At the measurement rate previously noted, the time required to make these measurements would exceed one hour and thirty minutes. Since catherization procedures involve risk to the patient, they are time critical. The inordinately long period of time that is needed to complete the diagnostic measurements using prior art sensors is outside acceptable medical standards. Although there are oxygen sensing devices that are presently available which are capable of operating at fast sampling rates, these devices suffer from the disadvantage of limited accuracy and the inability to measure gases.

SUMMARY OF THE INVENTION

It is an object of the present invention to provide an oxygen sensor which does not suffer from the heretofore mentioned disadvantages and limitations.

Another object of the present invention is to provide an oxygen sensor which rapidly and accurately measures oxygen contained in fluids and gases. Fluids include liquids such as human blood, artificial and synthetic blood, and animal blood. Gases include atmospheric air as well as inspired and expired air from a patient.

It is a further object of the present invention to provide an oxygen sensor for direct and continuous measurement of oxygen content in fluids and gases.

An oxygen sensor embodying the present invention is characterized by a sensor body with a chamber that houses an electrochemically active anode and an electrochemically active cathode. The cathode and anode are separated by a chemically inert, electrically inactive porous material which is in contact with both the anode and the cathode. An electrolytic solution saturates the porous material and makes electrical connection between the anode and cathode. An anode connector is in contact with the anode and a cathode connector is in contact with the cathode. An inlet port is provided for introducing a fluid or carrier gas containing the oxygen to be measured into the sensor body and an outlet port is provided for discharge of the fluid or gas. The electrolyte promotes catalytic reduction of free oxygen molecules carried by the fluid. The magnitude of current flow through a resistive load connected between the anode and cathode is directly proportional to the quantity of oxygen present in the fluid.

The invention accordingly comprises the methods and apparatuses together with their steps, parts, elements and interrelationships that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
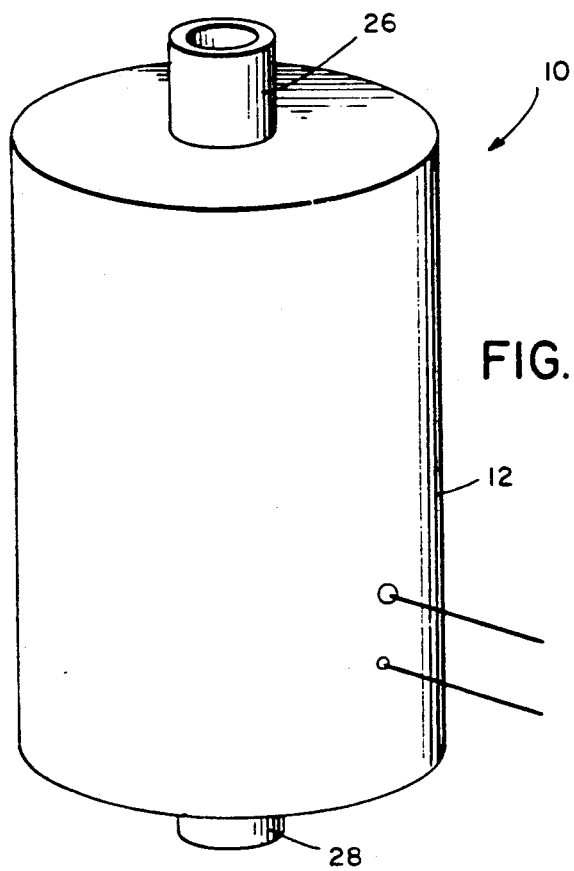
FIG. 1 is a perspective view of an oxygen sensor embodying the invention.

Referring now to the drawings, particularly FIG. 1, there is shown a sensor 10 embodying the present invention for measuring oxygen content of fluids and gases. In a medical application, sensor 10 is used for measuring oxygen content of a body fluid such as blood. In a commercial application, sensor 10 is used to measure oxygen content of a fluid or gas in a controlled environment.

Figure 2:
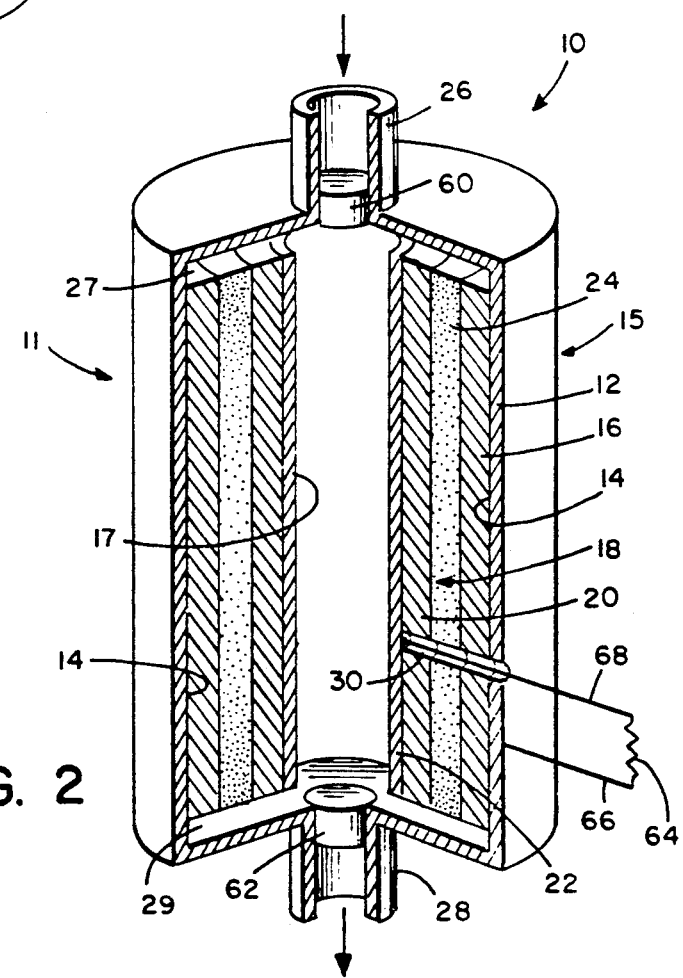
FIG. 2 is a perspective, partially cut-away view of the oxygen sensor of FIG. 1.

As best shown in FIG. 2, sensor 10 is a sealed or closed unit and includes an outer shell 11 in the form of a chemically inert, electrically conductive, substantially tubular anode connector 12 which forms a closed or sealed body having an inner chamber 14 in which there is housed an anode assembly 15 and a cathode assembly 17, a porous material 18 sandwiched between the anode and cathode assemblies. Anode assembly includes an anode electrode material 16 and anode connector 12. Anode material 16 is disposed within chamber 14 in contact with anode connector 12. Porous material 18 is a chemically inert, electrically inactive porous solid material in tubular form that is positioned inside anode electrode material 16 in physical contact therewith and separates anode assembly 15 from cathode assembly 17.

Cathode assembly 17 includes a cathode material 20 and a cathode connector 22. Cathode material 20, a material which is characterized by its ability to consume electrons by catalyzing the reduction of molecular oxygen to divalent negative oxygen ions, is a tubular member that is concentrically positioned within porous material 18. Anode material 16 and cathode material 20 are in intimate physical contact with porous material 18. That is, porous material 18 is sandwiched between and in contact with the inner surface of anode material 16 and the outer surface of cathode material 20. A chemically inert, electrically conductive tubular cathode connector 22 is in electrical contact with the cathode material 20. An electrolytic solution 24 saturates porous material 18 and wets both anode electrode material 16 and cathode material 20, thereby establishing an electrical path between the anode electrode material and the cathode electrode material via the pores in the porous material 18 which physically separates the anode material and the cathode material.

An inlet 26 at one end of sensor body 11 is provided for the introduction of a fluid or carrier gas containing oxygen from a sample to be measured into a chamber 27 of sensor 10 and a chamber 29 which leads to an outlet 28 at an opposite end of the sensor body is provided for the egress of the fluid or gas. A sealable electrical feedthrough 30 is provided to enable an electrical connection from cathode connector 22 to the outside of closed chamber 14. That is, both anode connector 12 and cathode connector 22 are available at the exterior of sensor body 11 without exposing chamber 14 to outside air. Accordingly, sealable feedthrough 30 is needed to maintain the integrity of sealed chamber 14.

In the illustrated embodiment, by way of example, anode connector 12 is a tubular, electrically conductive, chemically inert connector which is in contact with tubular electrochemically active anode material 16. Anode material 16 is composed of a material which is selected from a group of materials which form oxides of moderate thermodynamic stability and which liberate electrons during oxidation. An example of electrochemically active anode material 16 is cadmium, preferably in a form having large area to volume ratio, for example sponge or material plated on an inert reticulated support. It is believed that other suitable electrochemically active materials for use as anode material 16 include metals from the same chemical group as cadmium (group IIb, comprising zinc, cadmium, and mercury), as well as group VIII metals such as iron, ruthenium, and osmium, and metalloids such as arsenic, antimony, and bismuth. Preferably, such other materials are in a form having large area to volume ratio, such as sponge or material plated on an inert reticulated support, for example.

An example of suitable electrically conductive, chemically inert anode connector 12 for use in sensor 10 is copper metal plated with nickel. It is believed that other suitable electrically conductive, chemically inert contact materials for use in sensor 10 are brass plated with nickel or carbon or stainless steel.

In the illustrated embodiments, by way of example, chemically inert, electrically inactive porous solid material 18 is in tubular form and is a non-woven fabric composed of a plastic such as polyamide or polypropylene. Porous material 18 is sandwiched between anode material 16 and cathode material 20. An outer surface of porous material 18 is in contact with an inner surface of anode material 16 and an inner surface of the porous material is in contact with an outer surface of cathode material 20. A suitable porous material 18 is, for example, a polyamide battery separator material having a resistivity of 0.3 megaohm per square centimeter.

Tubular cathode material 20, for example a tubular member, is selected from a group of materials which are characterized by their ability to consume electrons by catalyzing the reduction of molecular oxygen to divalent negative oxygen ions, the cathode material being placed within and in intimate physical contact with the porous material. An example of a suitable electrochemically active cathode material 20 includes a material chosen from the group consisting of gold, silver, platinum, palladium, rhodium, and iridium and carbon. In one embodiment, cathode material 20 is composed of a carbon fiber felt in the form of a non-woven cloth or reticulated structure having pores greater than 100 microns in size. The thickness of cathode material 20 is greater than 5 millimeters and less than 10 millimeters. Preferably, the thickness of cathode material 20 is 6.35 millimeters.

An example of the electrically conductive, chemically inert cathode connector 22, which is in intimate physical contact with the cathode material, 20 is nickel metal for example, a porous tubular nickel material. It is believed that other suitable electrically conductive, chemically inert cathode connector 22 materials are carbon or stainless steel.

Electrolytic solution 24, which serves to produce electrical contact between anode material 16 and cathode material 20 by wetting both the anode and cathode surfaces and filling the pores in the porous material 18, is an aqueous solution consisting essentially of potassium hydroxide (KOH) and a dissolved metal. In the preferred embodiment, electrolytic solution 24 is a solution consisting of approximately 24 grams of KOH dissolved in 100 milliliters of distilled water to which approximately 10 milligrams of aluminum metal has been added and allowed to react, thereby forming an aqueous solution containing both dissolved potassium and aluminum. The addition of metallic aluminum to the KOH electrolyte, which results in the presence of aluminum hydroxide in the electrolyte, serves to significantly increase the speed of response of sensor 10 by catalyzing the chemical reactions taking place. It is believed that any electrolyte which incorporates an alkali metal hydroxide or an alkaline earth hydroxide or a rare earth metal hydroxide can be used in solution 24. It has been found that high speed detection of oxygen is provided by use of electrolytic solution 24 and use of nickel-plated copper as the inactive material for anode connector 12.

One method of wetting the component parts of sensor 10 with the electrolytic solution 24 includes the steps of immersing the porous material 18 in the solution, permitting the porous material to absorb as much solution as it possibly can and allowing the excess solution to drain off freely. Then, the anode connector 12, anode material 16, porous material 18, cathode material 20 and cathode connector 22 are assembled. The electrolytic solution 24 flows into or onto both anode material 16 and cathode material 20 to complete an electrical path between the anode and cathode.

In an alternative method of wetting the component parts of sensor 10 with electrolytic solution 24, anode material 16 and the porous material 18 are assembled together and immersed in the electrolytic solution. Next, the excess solution is permitted to drain off freely. Finally, cathode material 16 and its associated chemically inert electrically conductive connector 22 are attached to the wetted assembly of anode material 16 and porous material 18.

The anode connector 12, anode material 16, the porous material 18, the cathode material 20, and the cathode connector 22 are assembled and held together mechanically by any convenient mechanical means (not shown) which is electrically non-conductive, such as a polyamide or polypropylene string, for example.

Figure 3:
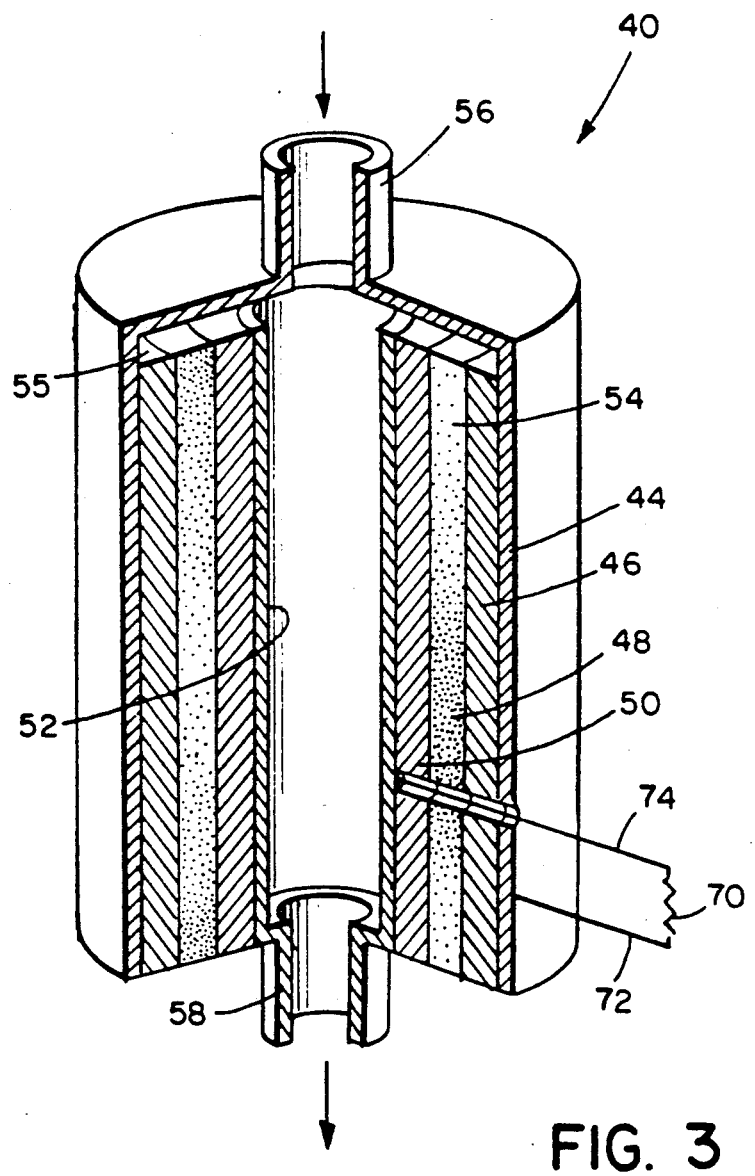
FIG. 3 is a perspective, partially cut-away view of an alternative embodiment of the invention.

Referring now to FIG. 3 there is shown an alternate embodiment of the invention in the form of a sensor 40 which is similar to sensor 10 with the exception that it is not a sealed unit. Sensor 40 includes an anode connector 44, an anode material 46, a porous separator 48, a cathode material 50, a cathode connector 52 and an electrolyte 54. The construction of sensor 40 and the component parts thereof are similar to the construction and components of sensor 10 with the exception that anode connector 44 does not form a closed chamber. An inlet 56 which leads to a chamber 55 is provided introducing a carrier gas into sensor 40 and an outlet 58 is provided for discharging of the carrier gas from the sensor. The carrier gas is a gas that is free of oxygen or a gas whose oxygen content is known.

In the embodiment of FIGS. 1 and 2, the anode connector or contact 12 encloses the entire sensor 10 and serves as a closed or sealed enclosure which is purged with an oxygen free gas, for example nitrogen, so that the components of the sensor are in an oxygen free environment. In this embodiment, a seal 60 is provided in inlet 26 and a seal 62 is provided in outlet 28 to permit introduction of a specimen to be analyzed into sensor 10 without contaminating chamber 14 with room air. As previously indicated, electrical contact to cathode connector 22, which must be brought to the exterior of sensor 10, is accomplished by means of electrical feedthrough 30 which is insulated with an appropriate chemically inert and non-conductive material, such as Apiezon W hard wax.

In the embodiment of non-sealed sensor 40 shown in FIG. 3, upon completion of the assembly procedure in the manner previously described in connection with sensor 10, sensor 40 is made ready for use by placing the sensor in a sealed enclosure (not shown). Provisions are made for making an electrical contact to each of the anode and cathode connectors 44 and 52, respectively, through the wall of the container. The container may be purged with an oxygen free gas, for example nitrogen, to remove oxygen from the components of the sensor.

No electrical charging of any kind is necessary during or after assembly of either sensor 10 or sensor 40 in order to make it suitable for use. When a suitable electrical load 64, for example a 22 ohm resistor, is placed across an anode lead 66 and a cathode lead 68 which are connected respectively to anode connector 12 and cathode connector 22, sensor 10 will provide an electrical current directly proportional to the quantity of oxygen present in a specimen which is introduced into chamber 14. Similarly, in the case of sensor 40, when a suitable electrical load 70, for example a 22 ohm resistor, is placed across an anode lead 72 and a cathode lead 74, current flowing through the resistor is directly proportional to the quantity of oxygen present in a specimen which is fed via a suitable conduit (not shown) such as glass or metal tubing for example, through the enclosure wall and into inlet 56 for passage through the sensor.

In operation of the invention, an oxygen free carrier gas, for example a gas containing 97% nitrogen, 2% hydrogen and 1% carbon monoxide is passed through a sample to be analyzed. Oxygen molecules from the sample are carried by the carrier gas and introduced into sensor 10 via inlet 26. The aluminum-modified KOH electrolytic solution 24 promotes the catalytic reduction of the free oxygen molecules admitted to the sensor 10 at cathode 20. In this electrochemical half-cell reaction, neutral oxygen is converted to divalent negative oxygen ions with the consumption of electrons supplied through the chemically inert, electrically conductive cathode connector 22 to the cathode material 20. At the same time, the oxygen potential of electrolytic solution 24 is raised by the presence of the excess oxygen ions so produced.

The electrochemical half-cell reaction at anode material 16 consists of the liberation of electrons by the anode material and the formation of positive ions of the anode material, which is consumed. These positive ions combine with divalent negative oxygen ions, which are provided by the excess oxygen potential of the aluminum-modified KOH electrolytic solution 24. Oxygen ions are not obliged to physically move through the electrolyte at a high speed in order to achieve high speeds of oxygen detection in sensor 10. This is demonstrated by the fact that sensor 10 response is not affected by variations in the thickness of the chemically inert electrically non-conductive porous solid separator material 18.

The electrons flow out of sensor 10 by way of chemically inert electrically conductive anode connector 12. Within a time period of 60 seconds from introduction of the carrier gas containing the oxygen from the specimen to be measured, sensor 10 generates a current which is directly proportional to the oxygen content of the specimen. The sensor made according to the teachings of the present invention is capable of measuring oxygen content in a 20 microliter air sample in 60 seconds.

It is to be understood that the sensor 40 operates in the same manner as that just described for sensor 10 with the exception that sensor 40 is placed in a sealed chamber that is purged of oxygen before the measurement cycle is started.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A sensor for the high speed detection of oxygen content in a fluid containing a specimen to be measured, said sensor comprising:
    (a) an electrochemically active anode material;
    (b) an electrochemically active cathode material;
    (c) a chemically inert, electrically inactive porous material disposed between and in contact with said anode and cathode materials, said porous material separating said anode material and said cathode material;
    (d) an aqueous electrolytic solution containing a potassium hydroxide electrolyte and a metal hydroxide, wherein said metal hydroxide is a material selected from a group consisting of aluminum hydroxide, an alkaline earth hydroxide and a rare earth metal hydroxide, said anode material, said cathode material and said porous material wetted by said aqueous electrolytic solution, an electrical path established between said anode material and said cathode material through said porous material;
    (e) first chemically inert, electrically conductive means in contact with said anode material; and
    (f) second chemically inert, electrically conductive means in contact with said cathode material.

2. The sensor as claimed in claim 1 wherein said cathode material is composed of a material which consumes electrons by catalyzing the reduction of molecular oxygen to divalent negative oxygen ions.

3. The sensor as claimed in claim 1 wherein said anode material is composed of a material which reacts to liberate electrons and forms an oxide of moderate thermodynamic stability.

4. The sensor as claimed in claim 1 wherein said electrolytic solution contains divalent oxygen ions.

5. The sensor as claimed in claim 1 wherein said first conductive means defines an outer shell which forms a sealed enclosure having an inner chamber, said anode material and said porous material and said cathode material disposed within said inner chamber.

6. The sensor as claimed in claim 5 including an inlet port and an outlet port formed in said outer shell, said inlet means configured to receive a specimen to be measured, said specimen enters said chamber through said inlet port and exits said chamber through said outlet port.

7. A sensor for measuring oxygen content of a specimen, said sensor comprising:
  (a) an electrochemically active anode means;
  (b) an electrochemically active cathode means;
  (c) a chemically inert, electrically inactive porous material sandwiched between and in contact with said anode means and said cathode means, said porous material separating said anode means and said cathode means;
  (d) an aqueous solution containing an electrolyte and a dissolved metal hydroxide, wherein said metal hydroxide is a material selected from a group consisting of aluminum hydroxide, an alkaline earth hydroxide and a rare earth metal hydroxide, said porous material wetted with said solution, an electrical path established between said anode means and said cathode means via said wetted porous material.

8. The sensor as claimed in claim 7 wherein said solution consists essentially of approximately 24 grams of potassium hydroxide dissolved in 100 milliliters of distilled water to which is added approximately 10 milligrams of the metal of said metal hydroxide.

9. The sensor as claimed in claim 8 wherein said metal is aluminum.

10. The sensor as claimed in claim 7 wherein said anode means is composed of a material which is selected from a group of materials which form oxides of moderate thermodynamic stability and which liberate electrons during oxidation.

11. The sensor as claimed in claim 7 wherein said cathode means is composed of a material which is selected from a group of materials which consume electrons by catalyzing the reduction of molecular oxygen to divalent negative oxygen ions.

* * * * *